(12) United States Patent
Schmidt et al.

(10) Patent No.: US 11,517,705 B2
(45) Date of Patent: Dec. 6, 2022

(54) APPARATUS AND METHOD FOR CALMING A BABY IN AN INTERIOR OF A VEHICLE

(71) Applicant: FORD GLOBAL TECHNOLOGIES, LLC, Dearborn, MI (US)

(72) Inventors: Eike Schmidt, Cologne (DE); Stefan Wolter, Würselen (DE)

(73) Assignee: FORD GLOBAL TECHNOLOGIES, LLC, Dearborn, MI (US)

( * ) Notice: Subject to any disclaimer, the term of this patent is extended or adjusted under 35 U.S.C. 154(b) by 917 days.

(21) Appl. No.: 16/288,153

(22) Filed: Feb. 28, 2019

(65) Prior Publication Data
US 2019/0275286 A1 Sep. 12, 2019

(30) Foreign Application Priority Data

Mar. 12, 2018 (DE) .......................... 102018203659.4

(51) Int. Cl.
| | |
|---|---|
| *A61M 21/02* | (2006.01) |
| *A61B 5/11* | (2006.01) |
| *B60N 2/28* | (2006.01) |
| *A61M 21/00* | (2006.01) |
| *B60N 2/00* | (2006.01) |
| *B60R 22/48* | (2006.01) |
| *A61B 5/318* | (2021.01) |
| *B60N 2/02* | (2006.01) |

(52) U.S. Cl.
CPC ............... *A61M 21/02* (2013.01); *A61B 5/11* (2013.01); *A61B 5/318* (2021.01); *B60N 2/002* (2013.01); *B60N 2/28* (2013.01); *B60R 22/48* (2013.01); *A61M 2021/0027* (2013.01); *A61M 2021/0061* (2013.01); *B60N 2002/0272* (2013.01); *B60R 2022/4816* (2013.01); *B60R 2022/4866* (2013.01)

(58) Field of Classification Search
CPC .................. A61M 21/00; A61M 21/02; A61M 2021/0005; A61M 2021/0027; A61M 2021/0061; B60N 2/002; B60N 2/028; B60N 2002/0272; B60N 2002/4816
See application file for complete search history.

(56) References Cited

U.S. PATENT DOCUMENTS

| | | |
|---|---|---|
| 6,004,259 A | 12/1999 | Sedaros |
| 7,039,207 B1 | 5/2006 | Elrod et al. |
| 7,464,424 B1 | 12/2008 | Formica et al. |

(Continued)

FOREIGN PATENT DOCUMENTS

KR 100727005 B1 6/2007

*Primary Examiner* — Carrie R Dorna
(74) *Attorney, Agent, or Firm* — Frank L. Lollo; MacMillan, Sobanski & Todd, LLC

(57) ABSTRACT

An apparatus for calming a baby in an interior of a vehicle has a heartbeat sensor device (11, 12, 13) configured to capture a heartbeat input signal that depends on the heartbeat of an occupant in an interior (18) of a vehicle (10). A heartbeat signal processing device (14) is configured to produce a heartbeat output signal that depends on the heartbeat input signal. A calming signal output device (15, 16, 17) is configured to output a calming signal that depends on the heartbeat output signal and that is perceivable by a baby in the interior (19) of the vehicle (10). The apparatus is to configured to output the calming signal, at least intermittently, directly during the capture of the heartbeat input signal.

19 Claims, 2 Drawing Sheets

(56) References Cited

U.S. PATENT DOCUMENTS

| | | |
|---|---|---|
| 7,510,521 B2 | 3/2009 | Bennett |
| 7,703,848 B1 | 4/2010 | Cochran et al. |
| 2010/0231014 A1 | 9/2010 | Gibree et al. |
| 2010/0253498 A1 | 10/2010 | Rork et al. |
| 2017/0119994 A1* | 5/2017 | Argaman ............. A61B 5/0205 |

* cited by examiner

APPARATUS AND METHOD FOR CALMING A BABY IN AN INTERIOR OF A VEHICLE

CROSS REFERENCE TO RELATED APPLICATIONS

This application claims priority to application DE102018203659.4, filed in the German Patent and Trademark Office on Mar. 12, 2018, which is incorporated herein by reference in its entirety.

STATEMENT REGARDING FEDERALLY SPONSORED RESEARCH

Not Applicable.

BACKGROUND OF THE INVENTION

The present invention relates in general to an apparatus for calming a baby in an interior of a vehicle, and, more specifically, to a vehicle having a suitable apparatus for reproducing calming sounds to be played for a baby.

While some babies easily relax and sometimes also fall asleep during car journeys, such journeys can cause great stress and excitement in other babies and are not perceived as comfortable. This can lead to very stressful car journey experiences for the baby and also their parents, in particular for the driver of the vehicle as well.

Moreover, safety reasons dictate that a baby spends the journey in a suitable baby seat or infant seat, the position of which is often located on one of the rear seats in the interior of the vehicle, and therefore spends the journey slightly isolated from its parents, particularly if only one parent is present, who is seated in the driver's seat in order to control the vehicle. This at least perceived lack of proximity to a parent can, in turn, be perceived as stress and can likewise contribute to making the journey uncomfortable for the baby and the parent.

Moreover, the bond between babies and parents develops further in the first months of life. Particularly in the case of frequent car journeys, the repeated feeling of a baby of being separated from its parents may lead to the bond not developing in a completely ideal manner.

What can be exploited to calm babies is that the heart sounds of the mother, which are already familiar since pregnancy, can have a calming effect on babies, e.g., infants in the first months of life.

Therefore, stored heart sounds of the mother used to calm the baby are disclosed in U.S. Pat. No. 7,464,424 B1. A baby calming system is disclosed, in which provision is made for heart sounds of the mother to be recorded with the aid of a stethoscope having a microphone and for said heart sounds to be played to the baby via a loudspeaker following an activation by way of the baby screaming or particularly loud ambient sounds.

U.S. Pat. No. 7,464,424 B1 discloses a holding apparatus for a baby in the form of a female upper body, in which, inter alia, an artificial heartbeat played to the baby is used for calming purposes.

U.S. Pat. No. 7,510,521 B2 discloses a playback device, housed in a stuffed animal, for example, for previously recorded sounds and for heart sounds of the mother, which are played back after an audio-based activation by the baby.

U.S. Pat. No. 7,039,207 B1 describes an entertainment and calming system in a baby seat, i.e., a vehicle seat for babies, in which, in addition to the playback of music, provision is also made for a synthetic heartbeat to be produced after activation by the baby or the driver of the vehicle.

US 2010/0231014 A1 discloses a child seat for automobiles, in which a vibration unit causes vibrations with a preset frequency for the purposes of calming the child, said frequency approximately corresponding to the heart rate, i.e., the frequency of the heartbeat, of a relaxed adult human.

However, the calming effect of heart sounds is not necessarily used to the full extent if these are not the heart sounds of the parents, in particular of the mother, and there has been no consideration for the fact that the profile of the heartbeat depends on the situation during which the recording was made. The baby or child also continuously perceives events in its surroundings. If the heart sounds or other calming signals are completely decoupled therefrom and if they have no relationship to the current situation because they were recorded at a different time and possibly recorded in a completely different state of tension, this may lead to the calming effect not occurring or only occurring to a reduced effect if this discrepancy is perceived by the baby.

SUMMARY OF THE INVENTION

It is an object of the present invention to provide an improved option for creating a calming atmosphere for a baby in a baby seat during the journey in a vehicle with at least one parent as a further occupant and, simultaneously, for strengthening the parent-child bond.

According to a first aspect of the invention, an apparatus for calming a baby in an interior of a vehicle comprises i) a heartbeat sensor device, configured to capture a heartbeat input signal that depends on the heartbeat of an occupant in an interior of a vehicle, ii) a heartbeat signal processing device, configured to produce a heartbeat output signal that depends on the heartbeat input signal, and iii) a calming signal output device, configured to output a calming signal that depends on the heartbeat output signal and that is perceivable by a baby in the interior of the vehicle. The apparatus is configured to output the calming signal, at least intermittently, substantially simultaneously with the capture of the heartbeat input signal.

The apparatus offers the option of using the heartbeat sensor device to establish the heartbeat, i.e., a heartbeat signal which indicates the individual heartbeats or contractions of the heart, at least over a period of time, of an occupant, i.e., a person in the interior of the vehicle, preferably a parent, and in particular the mother. To this end, a heartbeat input signal is captured. Depending on the employed sensor, this may either directly represent the heartbeat or contain information, for example video information, from which a representation of the heartbeat can be established. Here, a sensor that captures the pulse of the occupant, i.e. their heart rate, is also a heartbeat sensor which may be used to establish the heartbeat signal.

A vehicle is a motor vehicle in particular, for example an automobile, independently of the type of drive (i.e., electric vehicle or gas combustion vehicle). An occupant of a vehicle is a person in the interior of the vehicle (apart from the baby), whose heartbeat is captured.

If they are spatially separated, the heartbeat sensor device, the heartbeat signal processing device and the calming signal output device are directly or indirectly linked to one another in wired or wireless fashion using suitable interfaces, for example via a wireless local network, Bluetooth or other near field communication, wherein the heartbeat signal processing device may also be an integral constituent of the heartbeat sensor device or of the calming signal output device.

Depending on the input and output signals required for the respective embodiments, the signal processing carried out by the heartbeat signal processing device consists of conducting and optionally converting the heartbeat input signal into the heartbeat output signal and/or filtering and/or generating the heartbeat output signal from the information obtainable from the heartbeat input signal. To this end, the heartbeat signal processing device then comprises suitable means for carrying out the signal processing, for example a processor and a memory containing program code that, when executed by the processor, prompts the latter to implement the necessary signal processing (e.g., to synthesize heartbeats from the input signal).

While the heartbeat output signal may be an analog or digital electrical signal, the calming signal is, in particular, a signal that is perceivable by a baby or infant in the vehicle, said calming signal being generated by the calming signal output device from the heartbeat output signal. By way of example, the calming signal is perceivable as an audible acoustic signal. In a further embodiment, said signal may alternatively or additionally also be perceivable as a vibration signal. If the calming signal is audible, the calming signal output device comprises, for example, at least one loudspeaker, headphones, or other electroacoustic transducers, or an interface for connecting same.

The fact that the apparatus for calming a baby in an interior of a vehicle is configured to output the calming signal, at least intermittently, substantially simultaneously (i.e., directly) during the time of capturing of the heartbeat input signal offers the advantage that the heartbeat input signal captured from the occupant, for example the mother of the baby, has a temporal relationship with the current situation, in which the baby is, too, for which the calming signal is destined, and so the feeling of connectedness and of currently not being isolated is also amplified for the baby.

The fact that the calming signal is output directly during the capture of the heartbeat input signal denotes, in particular, a "live" mode, in which there is a real-time reproduction of the calming signal during the capture of the heartbeat input signal. The phrase "at least intermittently" includes the calming signal being output continuously during the capture of the heartbeat input signal, but also that provision can be made in one embodiment for the capture of the heartbeat input signal and/or the output of the calming signal only to be carried out simultaneously after a trigger signal or start, for example by the occupant or by the baby.

In one embodiment, the heartbeat sensor device comprises at least one first sensor in a seat of the vehicle. Preferably, this relates to one or more capacitive or electrical sensors in the seat of the occupant whose heartrate should be captured. In particular, such a sensor can be provided integrated in the driver's seat, but also in the front passenger seat and/or in other seats in the interior of the vehicle. Firstly, this offers the advantage of the sensor being integrated in a secured and protected manner in the vehicle and consequently of fewer accessories, which may be forgotten or damaged, being required for operating the apparatus. Secondly, this allows the heartbeat of an occupant of the vehicle to be captured without the latter having to put on a measuring appliance for this purpose.

In a further embodiment, provision is made for the heartbeat sensor device to alternatively or additionally comprise at least one second sensor in a steering wheel of the vehicle. Since the skin of the hands of the driver is in direct contact with the steering wheel of the vehicle, a sensor arranged in the steering wheel, for example one or more capacitive or electrical sensors, can very accurately capture the heart rate. Moreover the sensor is integrated in a secured and protected manner in the vehicle in this case, too, and it can supply a signal without the occupant, in this case the driver of the vehicle, having to put on or attach a measuring device.

The heartbeat sensor device may comprise a plurality of sensors that capture a heartbeat input signal in the same way or in different ways. The use of a plurality of signal sources offers the advantage that, for example, the heartbeat signal processing device selects the signal that was recorded best without interference or that a signal that has had the interference suppressed can be calculated.

In a further embodiment, the heartbeat sensor device comprises at least one microphone. By way of example, this relates to a microphone, integrated into the seat or the trim of the vehicle interior, with a sufficient sensitivity for recording minor variations in a frequency range of the human pulse. To this end, the associated heartbeat signal processing also comprises, in particular, filters to filter out the heartbeat signal from other noises in the vehicle interior. In this embodiment, the heartbeat input signal can advantageously be captured without the occupant having to put on a measuring appliance and, in this case, too, the sensor may be integrated in the vehicle in a secured and protected manner. In an alternative exemplary embodiment, provision can instead also be made for a small portable microphone to be applied to the body of the occupant, preferably in the region of the heart, said microphone transferring the captured signal to a receiver in the interior of the vehicle, for example in wireless fashion by near field communication. This offers the advantage of the quality of the captured signal being able to be improved by way of a suitable selection of the position of the microphone.

In one embodiment, the heartbeat sensor device comprises at least one portable heartbeat measuring appliance. Here, this may be a portable pulse measuring device or a "wearable computer" or, briefly, a "wearable", i.e., a portable computer system which is fastened during the application on the body of the user, in this case the occupant of the vehicle, and which comprises means, e.g. on the wrist or with the aid of a sensor chest band, for capturing a heartbeat input signal and for, moreover, transferring the captured heartbeat input signal data to the heartbeat signal processing device via a preferably wireless data interface. Alternatively, the functionality of the heartbeat signal processing device is also implemented in the portable heartbeat measuring appliance such that the heartbeat output signal is output directly.

In one embodiment, the heartbeat signal processing device comprises a means for amplifying the heartbeat input signal in order to produce the heartbeat output signal. By way of example, the amplification in this case relates to an amplification of the signal amplitude or the signal power, for example using an analog or digital amplifier circuit appropriate for the presence of an analog or digital electrical heartbeat input signal. In this way, improved noise suppression, for example, can be facilitated and the requirements on the calming signal output device can be reduced.

In a further embodiment, the heartbeat signal processing device comprises a means for establishing a frequency of the captured heartbeat input signal. In an exemplary embodiment, establishing the frequency of the captured heartbeat input signal or heart rate includes capturing the frequency curve over time and consequently also the changes therein.

If the frequency of the captured heartbeat input signal is established, provision is made in an exemplary embodiment for the heartbeat signal processing device to be configured to synthesize the heartbeat output signal on the basis of the established frequency. Instead of improving the input signal itself by way of suitable filtering measures, a new, synthetic heartbeat output signal is produced instead, said synthetic heartbeat output signal, for example, being optimized for the production of a suitable calming signal therefrom by way of the calming signal output device.

In an even further embodiment, provision is made for the heartbeat sensor device to comprise at least one camera sensor that is alignable to view the face of the occupant. Depending on the embodiment, this relates to a camera sensor for visible light or infrared light, wherein video sequences are recorded as heartbeat input signal, said video sequences at least also showing the face of the occupant or a region of the face. By way of example, this offers the advantage that video images of a camera, which may already be present in any case for other drivers assistance systems, by means of which the tiredness of the driver, for example, should be monitored, can also be used to supply video images allowing the identification of color and/or brightness variations therein by way of a continuous video analysis and the determination of the heart rate therefrom.

To this end, the heartbeat signal processing device is configured in an exemplary embodiment to identify in a curve of the heartbeat input signal over time a change, caused by the heartbeat, in a color and/or brightness, at least in a region of the face of the occupant of the vehicle, and to establish the heartbeat output signal therefrom. To this end, the heartbeat signal processing device has image or video analysis means, for example a processor and memory with a program code that, when executed by the processor, programs the latter to implement the described video analysis. Either a heartbeat output signal is established directly or the parameters for synthesizing a heartbeat output signal are established by determining the frequency of the color or brightness variations.

In one embodiment, the heartbeat signal processing device is configured to filter the heartbeat output signal depending on a gradient of a frequency curve of the heartbeat output signal. Although it is desirable for the curve of the heartbeat output signal, on which the output calming signal is based, to include the current common perception of the ambient situation for the occupant and the baby, i.e., for example, a situation-related increase in the frequency and a drop-off, which signals calming again, provision is made in this embodiment for the signal to be additionally filtered in order to filter out or attenuate frequency curves signaling danger or fear. By way of example, provision can be made for the heartbeat output signal to be intermittently masked, subjected to low-pass filtering or replaced by a buffer stored or synthetically generated signal with a lower frequency in the case of a frequency increase exceeding a predetermined threshold, for example on account of a sudden moment of shock for the occupant. This ensures that a calming signal can always be produced from the heartbeat output signal, said calming signal in fact promoting the calmness and the feeling of security for the baby.

In one embodiment, the heartbeat output device comprises a plurality of loudspeakers of the vehicle and a control unit, configured to emit the calming signal, which is perceivable by the baby in the vehicle, in a directly directed manner on a region of the interior of the vehicle provided for the baby. Thus, provision is made for the calming signal to be emitted as "directional audio", i.e., a directed audio signal, to the space occupied by the baby, which is usually predetermined by the position of the baby seat. By way of example, a directed audio signal is produced by suitable actuation of the loudspeakers such that a region in which the audio signal is easily perceivable is produced by the superposition of the audio signals, said audio signal at the same time being damped or canceled for the remaining regions. By way of example, this firstly offers the advantage that the calming signal only reaches the baby in the interior, while other occupants do not hear, or only hardly hear, the latter and possibly do not consider it bothersome themselves. Secondly, loudspeakers normally distributed across the interior of the vehicle can be used in this embodiment. In an embodiment in which the heartbeat sensor device and the heartbeat signal processing device, too, are realized by components of the vehicle, an apparatus for calming a baby is consequently available in an interior of a vehicle, said apparatus having been realized entirely by onboard means. Consequently, the parents need not purchase and set up a system that is at least partly separate from the vehicle and the parents have the option of choosing any seat when selecting a baby seat. Therefore, they require neither a specific model and nor need they carry out retrofitting of a possibly already present baby seat themselves.

In a further embodiment, the heartbeat output device comprises at least one loudspeaker that is integrated in a baby seat. In this way, the source of the calming signal is in the proximity of the ears of the baby, and so an exact alignment of the audio emission is not required. In this embodiment, the loudspeaker is connected to the heartbeat signal processing device. The connection can be implemented in wired fashion but also, in particular, wirelessly, for example by way of a wireless local network (WLAN), Bluetooth or other near field communication.

In an even further embodiment, the heartbeat output device, alternatively or additionally, comprises headphones. In a first exemplary embodiment, the headphones are adapted to the baby in order thus to allow the baby to be supplied with the calming signal sound in the most direct manner. In particular, provision can also be made in this exemplary embodiment for the heartbeat signal processing device and/or the heartbeat output device to be used to check and ensure that a maximum admissible volume is not exceeded. In a second exemplary embodiment, the headphones are deployed for the occupant of the vehicle in order to monitor the calming signal output to the baby via further headphones for the baby or via any other way, for example by way of loudspeakers in the baby seat. The connection can be implemented in wired fashion but also, in particular, wirelessly via WLAN, Bluetooth or other near field communication.

According to a second aspect of the invention, a vehicle comprises an apparatus according to the first aspect of the invention for calming a baby in an interior of the vehicle. According to a third aspect of the invention, a method for calming a baby in an interior of a vehicle comprises capturing a heartbeat input signal that depends on the heartbeat of an occupant in an interior of a vehicle using a heartbeat sensor device, producing a heartbeat output signal that depends on the heartbeat input signal using a heartbeat signal processing device, and outputting a calming signal that depends on the heartbeat output signal and that is perceivable by a baby in the interior of the vehicle using a calming signal output device, wherein outputting of the calming signal is implemented, at least intermittently, substantially simultaneously with the capture of the heartbeat input signal. In this way, the advantages and peculiarities of the apparatus according to the invention for calming a baby in an interior of a vehicle are also implemented within the scope of a vehicle and a suitable operating method.

Further advantages of the present invention will become clear from the detailed description and the figures. The invention is explained in more detail below in conjunction with the following description of exemplary embodiments, with reference being made to the attached figures.

DETAILED DESCRIPTION OF PREFERRED EMBODIMENTS

It is understood that other embodiments can be used and structural or logical changes can be implemented without deviating from the scope of protection of the present invention. It is understood that the features of the various exemplary embodiments described above and below can be combined with one another, provided nothing else is specifically specified. Therefore, the description should not be construed as having a limiting effect and the scope of protection of the present invention is defined by the attached claims.

Figure 1:
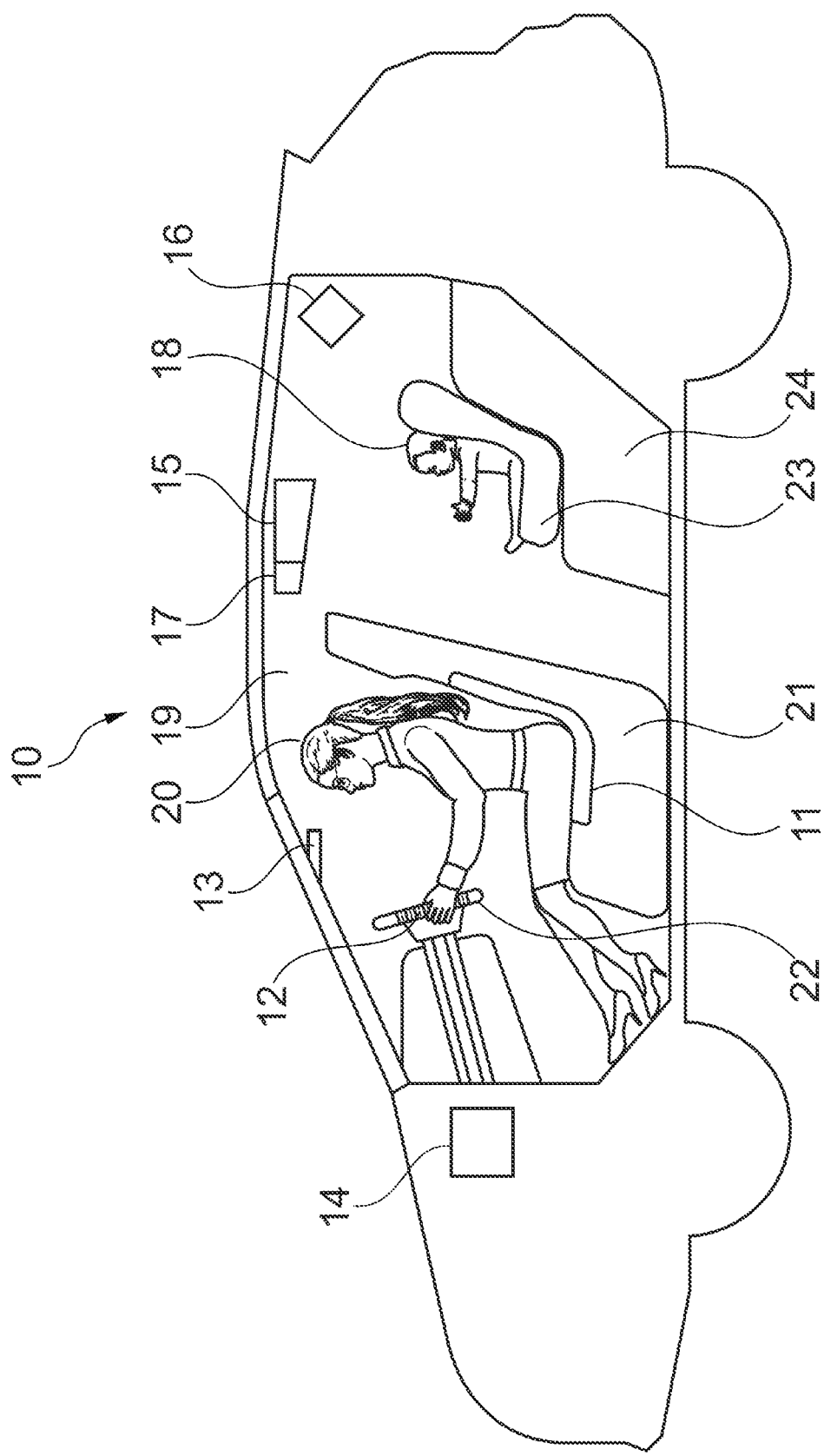
FIG. 1 is a schematic illustration of an example of a vehicle having an apparatus for calming a baby in an interior of a vehicle according to first embodiment of the invention.

FIG. 1 shows a schematic illustration of an example of a vehicle 10 having an apparatus 11, 12, 13, 14, 15, 16, 17 for calming a baby 18 in an interior 19 of the vehicle 10 according to first embodiment of the invention. The vehicle 10 has an apparatus 11, 12, 13, 14, 15, 16, 17, which comprises a heartbeat sensor device 11, 12, and/or 13, configured to capture a heartbeat input signal that depends on the heartbeat of an occupant 20 in the interior 19 of the vehicle 10. In the shown embodiment, the heartbeat sensor device 11, 12, 13 has a combination of a plurality of sensors in order to capture the heartbeat of the occupant 20, in this case the driver of the vehicle 10. Even though no explicit distinction is made between male and female occupant, the phrase "occupant" always relates to the person whose heartbeat should be captured, independently of their sex. Further persons, not shown here, whose heartbeat is not captured may be situated elsewhere in the vehicle 10. The heartbeat of the occupant 20 is captured, firstly, via a sensor signal of a first sensor 11 in the driver's seat 21. Secondly, the steering wheel 22 of the vehicle 10 also comprises a suitable second sensor 12. Additionally, a driver camera is provided as third sensor or camera sensor 13, said driver camera capturing the face of the occupant 20 on the driver's seat 21.

The sensors of the heartbeat sensor device 11, 12, 13 are connected to a heartbeat signal processing device 14 via a wireless connection, not shown. Heartbeat signal processing device 14 is configured to produce a heartbeat output signal that depends on the heartbeat input signal. In the shown embodiment, preliminary output signals are established first and an interference-free heartbeat output signal is then established therefrom for the sensor signals.

The heartbeat signal processing device 14 is connected via a wireless connection, not shown, to a calming signal output device 15, 16, and/or 17, configured to output a calming signal that depends on the heartbeat output signal and that is perceivable by the baby 18 in the interior 19 of the vehicle 10. In the shown embodiment, the calming signal output device 15, 16, 17 comprises at least a first loudspeaker 15 and a second loudspeaker 16 and a control unit 17. The calming signal is generated by the control unit 17 and emitted as a directed audio signal via the first loudspeaker 15 and the second loudspeaker 16 directly in the direction of the position of the baby seat 23 or infant seat, in which the baby 18 is situated and which is fastened to a rear seat 24 in the vehicle interior 19. Here, the apparatus is configured to output the calming signal, at least intermittently, directly during the capture of the heartbeat input signal. In another embodiment, the control unit 17 can also be, for example, a part of the heartbeat signal processing device 14.

In the illustrated embodiment, the apparatus is realized without any requirements in relation to the baby seat 23, and so any seat that is permissible as a baby seat is suitable for use with the described apparatus.

Figure 2:
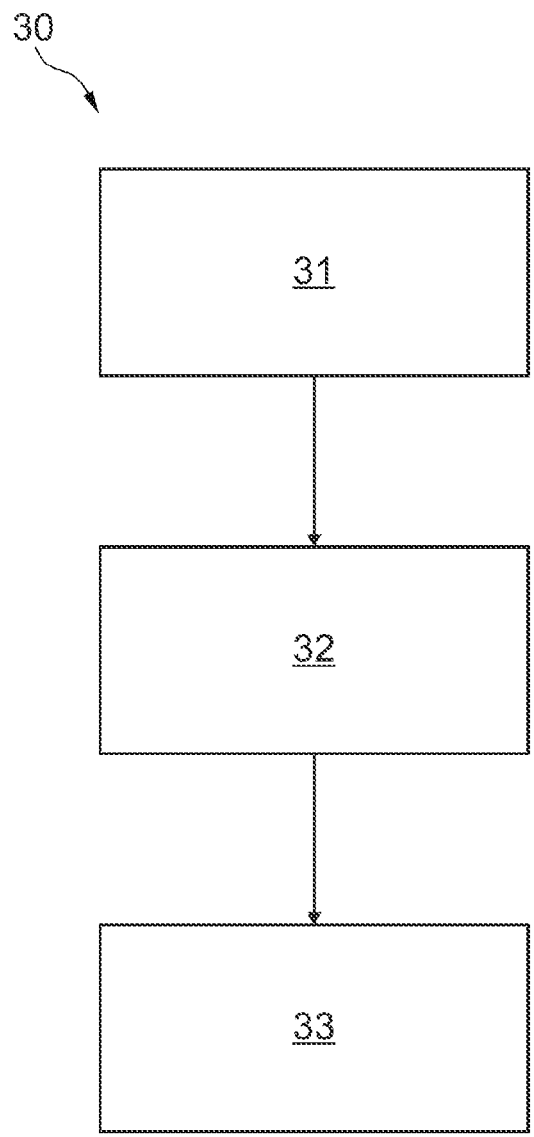
FIG. 2 is a schematic illustration of an example of a method for calming a baby in an interior of a vehicle according to a second embodiment of the invention.

FIG. 2 shows a schematic illustration of an example of a method for calming a baby in an interior of a vehicle according to a second embodiment of the invention. The shown method 30 comprises, in a first step 31, capturing a heartbeat input signal that depends on the heartbeat of an occupant in an interior of a vehicle using a heartbeat sensor device. In a second step 32, there is a production of a heartbeat output signal that depends on the heartbeat input signal using a heartbeat signal processing device. In a third step 33, there is an output of a calming signal that depends on the heartbeat output signal and that is perceivable by a baby in the interior of the vehicle using a calming signal output device. Output of the calming signal is implemented, at least intermittently, directly (i.e., substantially simultaneously) during the capture of the corresponding heartbeat input signal. Therefore, the shown sequence of steps only visualizes a basic progression of the method, without a step having to be already completed when a further step is carried out. Thus, for example, after capturing a first interval of the heartbeat input signal, the signal processing thereof and the production of an associated first interval of the heartbeat output signal can be implemented, from which, in turn, a first interval of the calming signal is generated and output while, at the same time, a second interval the heartbeat input signal is being captured. This "live" mode of operation can be implemented for a certain period of time or continuously.

Even though the invention was, in detail, described and illustrated more closely by the preferred exemplary embodiments, the invention is not limited by the disclosed examples and other variants can be derived herefrom by a person skilled in the art without departing from the scope of protection of the invention.

What is claimed is:

1. Apparatus for calming a baby in an interior of a vehicle, comprising:
    a heartbeat sensor device configured to capture a heartbeat input signal that correlates with an actual heartbeat of an occupant in the interior of the vehicle, wherein the heartbeat sensor device is embedded in a seat of the vehicle;
    a heartbeat signal processing device configured to produce a heartbeat output signal representative of the heartbeat of the occupant in response to the heartbeat input signal; and
    a calming signal output device configured to output a calming signal reproducing the heartbeat output signal and that is perceivable by a baby in the interior of the vehicle, wherein the calming signal is output at least intermittently and is output substantially simultaneously with the capture of the corresponding heartbeat input signal.

2. The apparatus as claimed in claim 1 wherein the heartbeat sensor device comprises at least one microphone.

3. The apparatus as claimed in claim 1 wherein the heartbeat sensor device comprises at least one portable heartbeat measuring appliance.

4. The apparatus as claimed in claim 1 wherein the heartbeat signal processing device comprises a means for amplifying the heartbeat input signal in order to produce the heartbeat output signal.

5. The apparatus as claimed in claim 1 wherein the heartbeat signal processing device establishes a frequency of the captured heartbeat input signal.

6. The apparatus as claimed in claim 5 wherein the heartbeat signal processing device is configured to synthesize the heartbeat output signal on the basis of the established frequency.

7. The apparatus as claimed in claim 1 wherein the heartbeat signal processing device is configured to filter the heartbeat output signal depending on a gradient of a predetermined frequency curve.

8. The apparatus as claimed in claim 1 wherein the calming signal output device comprises at least one loudspeaker that is integrated in a baby seat.

9. The apparatus as claimed in claim 1 wherein the calming signal output device comprises headphones.

10. Apparatus for calming a baby in an interior of a vehicle, comprising:
   a heartbeat sensor device configured to capture a heartbeat input signal that correlates with an actual heartbeat of an occupant in the interior of the vehicle, wherein the heartbeat sensor device is embedded in a steering wheel of the vehicle;
   a heartbeat signal processing device configured to produce a heartbeat output signal representative of the heartbeat of the occupant in response to the heartbeat input signal; and
   a calming signal output device configured to output a calming signal reproducing the heartbeat output signal and that is perceivable by a baby in the interior of the vehicle, wherein the calming signal is output at least intermittently and is output substantially simultaneously with the capture of the corresponding heartbeat input signal.

11. The apparatus as claimed in claim 10 wherein the heartbeat sensor device comprises at least one microphone.

12. The apparatus as claimed in claim 10 wherein the heartbeat sensor device comprises at least one portable heartbeat measuring appliance.

13. The apparatus as claimed in claim 10 wherein the heartbeat signal processing device comprises a means for amplifying the heartbeat input signal in order to produce the heartbeat output signal.

14. The apparatus as claimed in claim 10 wherein the calming signal output device comprises a plurality of loudspeakers of the vehicle and a control unit configured to emit the calming signal as audible sound perceivable by the baby in the vehicle, in a directly directed manner to a region of the interior of the vehicle occupied by the baby.

15. The apparatus as claimed in claim 10 wherein the calming signal output device comprises at least one loudspeaker that is integrated in a baby seat.

16. The apparatus as claimed in claim 10 wherein the calming signal output device comprises headphones.

17. Apparatus for calming a baby in an interior of a vehicle, comprising:
   a heartbeat sensor device configured to capture a heartbeat input signal that correlates with an actual heartbeat of an occupant in the interior of the vehicle, wherein the heartbeat sensor device comprises at least one camera sensor that is alignable to view the face of the occupant;
   a heartbeat signal processing device configured to produce a heartbeat output signal representative of the heartbeat of the occupant in response to the heartbeat input signal; and
   a calming signal output device configured to output a calming signal reproducing the heartbeat output signal and that is perceivable by a baby in the interior of the vehicle, wherein the calming signal is output at least intermittently and is output substantially simultaneously with the capture of the corresponding heartbeat input signal.

18. The apparatus as claimed in claim 17 wherein the heartbeat signal processing device is configured to identify a variation of the heartbeat input signal from the camera signal related to the heartbeat, wherein the variation occurs in a color or brightness in a region of the face of the occupant, and to establish the heartbeat output signal therefrom.

19. Apparatus for calming a baby in an interior of a vehicle, comprising:
   a heartbeat sensor device configured to capture a heartbeat input signal that correlates with an actual heartbeat of an occupant in the interior of the vehicle;
   a heartbeat signal processing device configured to produce a heartbeat output signal representative of the heartbeat of the occupant in response to the heartbeat input signal; and
   a calming signal output device configured to output a calming signal reproducing the heartbeat output signal and that is perceivable by a baby in the interior of the vehicle, wherein the calming signal is output at least intermittently and is output substantially simultaneously with the capture of the corresponding heartbeat input signal, wherein the calming signal output device comprises a plurality of loudspeakers of the vehicle and a control unit configured to emit the calming signal as audible sound perceivable by the baby in the vehicle, in a directly directed manner to a region of the interior of the vehicle occupied by the baby.

* * * * *